(12) United States Patent
Guo et al.

(10) Patent No.: US 12,171,564 B1
(45) Date of Patent: Dec. 24, 2024

(54) METHOD FOR DETECTING QRS COMPLEX OF ELECTROCARDIOGRAM SIGNAL, APPARATUS THEREFOR, DEVICE AND MEDIUM

(71) Applicant: Central South University, Changsha (CN)

(72) Inventors: Lin Guo, Changsha (CN); Nan Ma, Changsha (CN); Ying An, Changsha (CN); Qianyun Zhan, Changsha (CN); Jun Long, Changsha (CN)

(73) Assignee: Central South University, Changsha (CN)

( * ) Notice: Subject to any disclaimer, the term of this patent is extended or adjusted under 35 U.S.C. 154(b) by 0 days.

(21) Appl. No.: 18/818,084

(22) Filed: Aug. 28, 2024

(30) Foreign Application Priority Data

Jan. 24, 2024 (CN) .............................. 202410096841

(51) Int. Cl.
 *A61B 5/349* (2021.01)
 *A61B 5/00* (2006.01)
 *A61B 5/256* (2021.01)
 *G06N 3/045* (2023.01)

(52) U.S. Cl.
 CPC .............. *A61B 5/349* (2021.01); *A61B 5/256* (2021.01); *A61B 5/7225* (2013.01); *G06N 3/045* (2023.01)

(58) Field of Classification Search
 None
 See application file for complete search history.

(56) References Cited

U.S. PATENT DOCUMENTS

2021/0401376 A1* 12/2021 Roveda ................ A61B 5/7264
2022/0346885 A1* 11/2022 Kunio ................... G06T 7/0012

FOREIGN PATENT DOCUMENTS

| CN | 111184508 A | 5/2020 |
| CN | 116863939 A | 10/2023 |
| IN | 201921018639 A | 11/2020 |

OTHER PUBLICATIONS

First Office Action issued in 202410096841.0, and English Translation thereof, Mar. 5, 2024.
Notification to Grant Patent Right for Invention issued in CN202410096841.0, and English Translation thereof, Apr. 2, 2024.

* cited by examiner

*Primary Examiner* — Ankit D Tejani
(74) *Attorney, Agent, or Firm* — ARC IP Law, PC; Joseph J. Mayo

(57) ABSTRACT

A method for detecting a QRS complex of an electrocardiogram signal, an apparatus therefor, a device and a medium are provided. A QRS complex of an electrocardiogram signal is detected by a detection model including a DenseNet and a dual-channel Long Short-Term Memory (LSTM). Spatial feature information of the QRS complex in the electrocardiogram signal is learned through the DenseNet, and then the spatial feature learned by the DenseNet and the time sequence data are input into respective channels of the dual-channel LSTM, so that the dual-channel LSTM can fuse the spatial information and the time sequence information of the QRS complex in the electrocardiogram signal, thereby improving a segmentation effect of the model on features, and finally improving accuracy of detecting the QRS complex.

13 Claims, 5 Drawing Sheets

METHOD FOR DETECTING QRS COMPLEX OF ELECTROCARDIOGRAM SIGNAL, APPARATUS THEREFOR, DEVICE AND MEDIUM

CROSS-REFERENCE TO RELATED APPLICATION

This patent application claims the benefit and priority of Chinese Patent Application No. 202410096841.0 filed with the China National Intellectual Property Administration on Jan. 24, 2024, the disclosure of which is incorporated by reference herein in its entirety as part of the present disclosure.

BACKGROUND OF THE INVENTION

Technical Field of the Invention

The embodiment of the present disclosure relates to the technical field of processing an electrocardiogram signal, in particular to a method for detecting a QRS complex of an electrocardiogram signal, an apparatus therefor, a device and a medium.

Description of the Related Art

A QRS complex in an electrocardiogram signal provides abundant information about ventricular excitation and conduction and information about ectopic beat. The analysis of the QRS complex in an electrocardiogram time sequence can provide useful information for medical auxiliary diagnosis. The automatic and effective detection of the QRS based on a deep learning method can improve the rate of electrocardiogram analysis and reduce the burden on doctors; and can also help people find potential problems early, thereby reducing the mortality of cardiovascular diseases through early intervention and timely treatment.

However, the method for detecting the QRS based on the deep learning method has low detection performance due to reasons, such as complex signal shapes and individual differences of waveforms. Therefore, how to improve the accuracy of detecting the QRS complex based on the deep learning method is an urgent problem to be solved at present.

BRIEF SUMMARY OF THE INVENTION

An overview of the subject described in detail in the present disclosure is provided. The overview is not intended to limit the scope of protection of the claims.

The main purpose of the embodiment of the present disclosure is to provide a method for detecting a QRS complex of an electrocardiogram signal, an apparatus therefor, a device and a medium, which can improve the accuracy of detecting the QRS complex.

In order to achieve the above objective, a first aspect of an embodiment of the present disclosure proposes a method for detecting a QRS complex of an electrocardiogram signal, where the method includes:

acquiring time sequence data of an electrocardiogram signal from an electrocardiogram;

constructing a detection model comprising a DenseNet and a dual-channel Long Short-Term Memory (LSTM), inputting the time sequence data into the detection model to extract a spatial feature of the electrocardiogram signal from the time sequence data according to the DenseNet, inputting the time sequence data and the spatial feature into respective channels of the dual-channel LSTM, and detecting a QRS complex of the electrocardiogram signal by the dual-channel LSTM.

In some embodiments, the inputting the time sequence data and the spatial feature into respective channels of the dual-channel LSTM, and detecting a QRS complex of the electrocardiogram signal by the dual-channel LSTM, includes:

inputting the time sequence data into a first channel of the dual-channel LSTM to obtain a first feature output by the first channel, and inputting the spatial feature into a second channel of the dual-channel LSTM to obtain a second feature output by the second channel;

fusing the first feature and the second feature by means of respective attention weights by using an attention mechanism to obtain a third feature; where a sum of attention weights of two channels is equal to 1;

detecting the QRS complex according to the third feature.

In some embodiments, the detection model is trained by preprocessed training data; and preprocessing of training data includes:

normalizing the training data;

carrying out sample equalization for various labels on normalized training data;

carrying out data enhancement on the training data after sample equalization.

In some embodiments, the carrying out sample equalization of various labels on normalized training data includes:

repeating following steps until a predetermined data equalization degree is reached; the following steps include:

selecting minority category samples in the normalized training data;

randomly selecting a corresponding neighbor for each of the minority category samples, where the neighbor is one of several nearest neighbor samples of each of the minority category samples;

generating a new sample between each of the minority category samples and corresponding neighbor by a linear interpolation method.

In some embodiments, in training process, the detection model obtains the attention weights by the following equation:

$$\text{Attention}(H_{LSTM1}, H_{LSTM2}) = \text{softmax}(W \cdot \tanh(U \cdot H_{LSTM1} + V \cdot H_{LSTM2}));$$

where $H_{LSTM1}$ is an output feature of the first channel, $H_{LSTM2}$ is an output feature of the second channel, tanh is a hyperbolic tangent function, softmax( ) is an activation function, W, U, V are learnable weight parameters, and Attention($H_{LSTM1}$, $H_{LSTM2}$) is the attention weights;

in the training process, the detection model fuses the output feature of the first channel and the output feature of the second channel by following equation:

$$\text{Fused Feature} = \text{Attention}(H_{LSTM1}, H_{LSTM2}) \cdot H_{LSTM1} + (1 - \text{Attention}(H_{LSTM1}, H_{LSTM2})) \cdot H_{LSTM2};$$

where Fused Feature is a feature obtained by fusing the output feature of the first channel and the output feature of the second channel.

In some embodiments, a loss function of the detection model in the training process is:

$$L_{total} = L_{cls} + \lambda L_{reg};$$

$$L_{cls}(y_{cls}, \hat{y}_{cls}) = -(y_{cls} \cdot \log(\hat{y}_{cls}) + (1 - y_{cls}) \cdot \log(1 - \hat{y}_{cls}));$$

$$L_{reg}(t_{reg}, \hat{t}_{reg}) = \text{Smooth}L1(t_{reg} - \hat{t}_{reg});$$

where $L_{total}$ denotes a loss function of the detection model, $L_{cls}$ denotes a classification loss, $L_{reg}$ denotes a regression loss, $\lambda$ denotes a predetermined weight parameter, $\hat{y}_{cls}$ denotes the QRS complex detected by the detection model, $y_{cls}$ denotes a real category label, $\hat{t}_{reg}$ denotes a position of the QRS complex detected by the detection model, and $t_{reg}$ denotes a real position label.

In some embodiments, the training data is obtained by following steps:
  using a wearable electrocardiogram data acquisition device to acquire an original electrocardiogram signal of a user;
  using a high-pass filter to filter the original electrocardiogram signal;
  downsampling the original electrocardiogram signal filtered to obtain the training data.

In order to achieve the above objective, a second aspect of an embodiment of the present disclosure provides an apparatus for detecting a QRS complex of an electrocardiogram signal, where the apparatus includes:
  a data acquisition unit, configured to acquire time sequence data of an electrocardiogram signal from an electrocardiogram signal;
  a wave complex detection unit, configured to construct a detection model including a DenseNet and a dual-channel Long Short-Term Memory (LSTM), input the time sequence data into the detection model to extract a spatial feature of the electrocardiogram signal from the time sequence data according to the DenseNet, input the time sequence data and the spatial feature into respective channels of the dual-channel LSTM, and detect a QRS complex of the electrocardiogram signal by the dual-channel LSTM.

In order to achieve the above objective, a third aspect of an embodiment of the present disclosure provides an electronic device, including at least one control processor and a memory communicated with the at least one control processor; where instructions executable by the at least one control processor are stored in the memory, and the instructions are executed by the at least one control processor, so that the at least one control processor is capable of executing the method for detecting the QRS complex of the electrocardiogram signal.

In order to achieve the above objective, a fourth aspect of an embodiment of the present disclosure provides a computer-readable storage medium, where computer-executable instructions are stored in the computer-readable storage medium, and the computer-executable instructions are used to cause a computer to execute the method for detecting the QRS complex of the electrocardiogram signal.

An embodiment of the present disclosure provides a method for detecting a QRS complex of an electrocardiogram signal. According to the method, by using a detection model including a DenseNet and a dual-channel LSTM, spatial feature information of the QRS complex in the electrocardiogram signal is learned through the DenseNet, and then the spatial feature learned by the DenseNet and time sequence data are input into respective channels of the dual-channel LSTM, so that the dual-channel LSTM can fuse the spatial information and time sequence information of the QRS complex in the electrocardiogram signal, thereby improving a segmentation effect of the model on features, and finally improving an accuracy of detecting the QRS complex.

It can be understood that the beneficial effects of the second to fourth aspects mentioned above compared to the related art are the same as those of the first aspect mentioned above. Referring to the relevant description in the first aspect mentioned above, it will not be described in detail here.

BRIEF DESCRIPTION OF THE DRAWINGS

In order to explain the technical scheme in the embodiment of the present disclosure more clearly, the drawings that need to be used in the description of the embodiment or related technologies will be briefly introduced. Obviously, the drawings in the following description are only some embodiments of the present disclosure. For those skilled in the art, other drawings can be obtained according to these drawings without creative labor.

DETAILED DESCRIPTION OF THE INVENTION

In order to make the above objectives, the technical schemes and the advantages of the present disclosure more obvious and understandable, the present disclosure will be explained in further detail with reference to the drawings and the embodiments hereinafter. It should be understood that the specific embodiments described herein are only used to explain the present disclosure, rather than limit the present disclosure.

It should be noted that although the functional modules are divided in the schematic diagram of the apparatus and the logical order is shown in the flow chart, in some cases, the steps shown or described may be executed in an order different from the module division in the apparatus or in the flow chart. The terms "first" and "second" in the specification and claims and the above drawings are used to distinguish similar objects, and are not necessarily used to describe a specific order or sequence.

Unless otherwise defined, all technical and scientific terms used herein have the same meaning as commonly understood by those skilled in the technical field of the present disclosure. The term used herein is only for the purpose of describing the embodiments of the present disclosure, and is not intended to limit the present disclosure.

A QRS complex in an electrocardiogram signal provides abundant information about ventricular excitation and conduction and information about ectopic beat. The analysis of the QRS complex in an electrocardiogram time sequence can provide useful information for medical auxiliary diagnosis. The automatic and effective detection of the QRS based on a deep learning method can improve the rate of electrocardiogram analysis and reduce the burden on doctors; and can also help people find potential problems early, thereby reducing the mortality of cardiovascular diseases through early intervention and timely treatment.

However, the method for detecting the QRS based on the deep learning method has low detection performance due to reasons, such as complex signal shapes and individual differences of waveforms. Therefore, how to improve the accuracy of detecting the QRS complex based on the deep learning method is an urgent problem to be solved at present.

Figure 1:
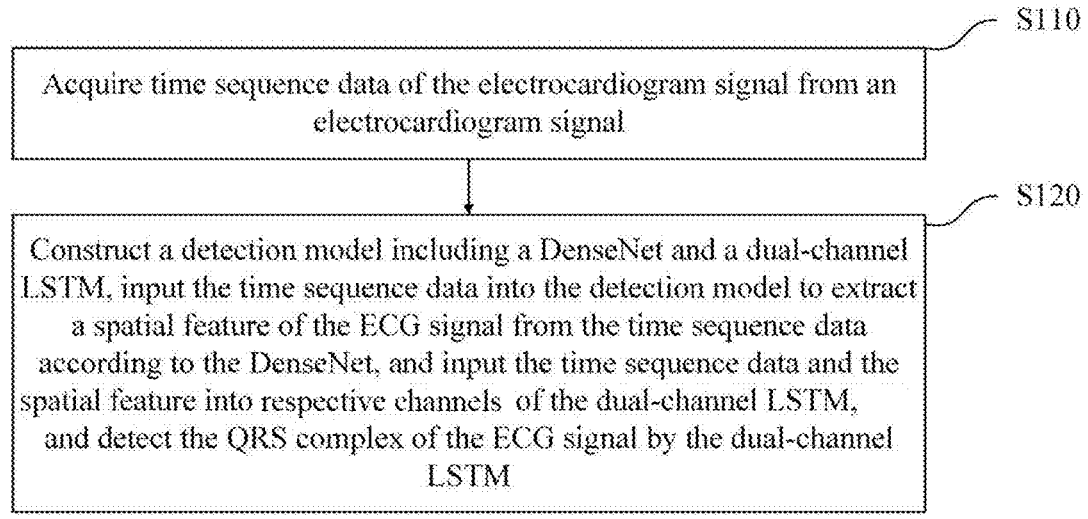
FIG. 1 is a flow chart of a method for detecting a QRS complex of an electrocardiogram signal according to an embodiment of the present disclosure.

In order to solve the above technical defects, referring to FIG. 1, an embodiment of the present disclosure provides a method for detecting a QRS complex of an electrocardiogram signal. The method for detecting the QRS complex of the electrocardiogram signal includes Step S110 and Step S120.

Step S110, time sequence data of the electrocardiogram signal is acquired from an electrocardiogram signal.

Step S120, a detection model including a DenseNet and a dual-channel Long Short-Term Memory (LSTM) is constructed. In some embodiments, the detection model is consisted of a DenseNet and a LSTM. The time sequence data is input into the detection model to extract a spatial feature of the electrocardiogram signal from the time sequence data according to the DenseNet, and the time sequence data and the spatial feature are input into respective channels of the dual-channel LSTM, and the QRS complex of the electrocardiogram signal is detected by the dual-channel LSTM.

The time sequence data of the electrocardiogram signal is mainly the numerical data of the electrocardiogram signal extracted from the electrocardiogram. The DenseNet refers to a dense convolution network, which makes full use of all the features in training process by a connecting all previous layers and subsequent layers densely, so as to achieve better results and reduce parameters. The dual-channel LSTM can process the input sequences of different channels in parallel by increasing input channels of the LSTM, to speed up the training, and can capture the context information in the sequence from more dimensions, thereby enhancing the expression ability of the model.

In this embodiment, a detection model includes a DenseNet and a dual-channel Long Short-Term Memory (LSTM), spatial feature information of the QRS complex in the electrocardiogram signal is learned through the DenseNet, and then the spatial feature learned by the DenseNet and time sequence data are input into respective channels of the dual-channel LSTM, so that the dual-channel LSTM can fuse the spatial information and time sequence information of the QRS complex in the electrocardiogram signal, thereby improving a segmentation effect of the model on features, and finally improving an accuracy of detecting the QRS complex.

Figure 2:
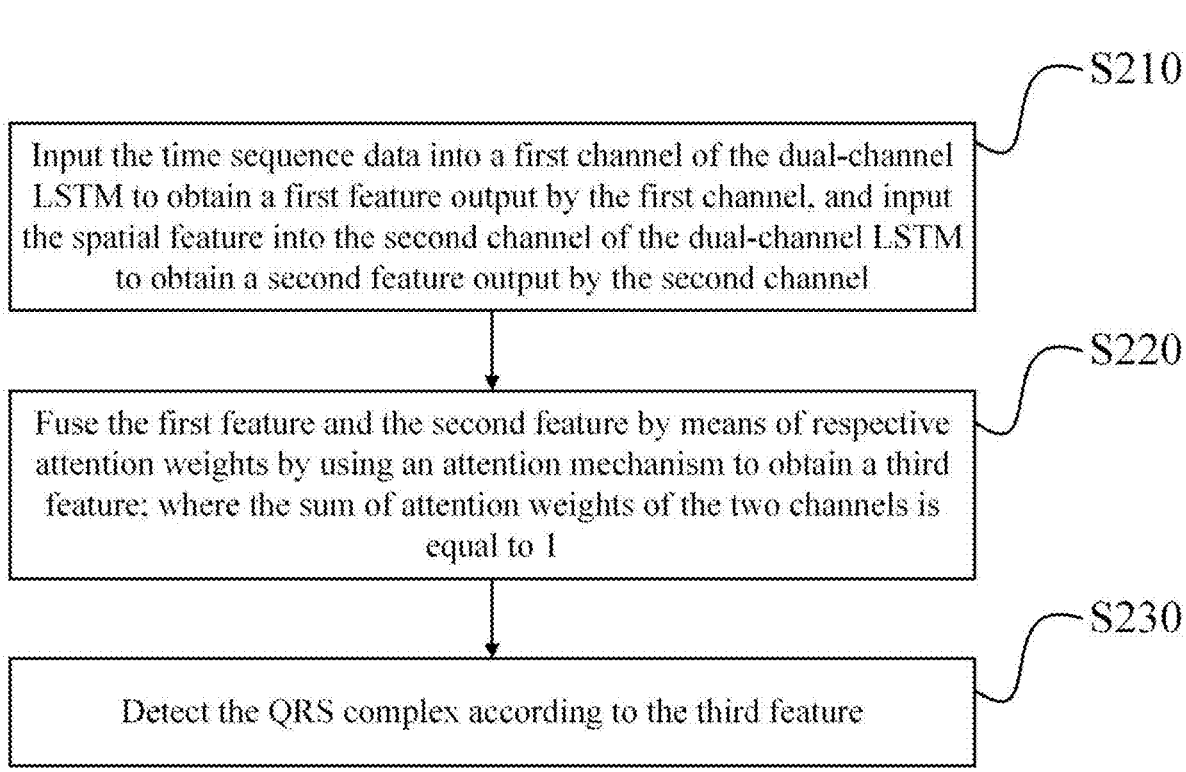
FIG. 2 is a schematic flow chart of detecting a QRS complex of an electrocardiogram signal by a dual-channel LSTM according to an embodiment of the present disclosure.

As shown in FIG. 2, in some embodiments of the present disclosure, the step of inputting the time sequence data and the spatial feature into respective channels of the dual-channel LSTM, and detecting the QRS complex of the electrocardiogram signal by the dual-channel LSTM in Step S120, includes Step S210 to Step S230.

Step S210, the time sequence data is input into a first channel of the dual-channel LSTM to obtain a first feature output by the first channel, and the spatial feature is input into the second channel of the dual-channel LSTM to obtain a second feature output by the second channel.

Step S220, the first feature and the second feature are fused by means of respective attention weights by using an attention mechanism to obtain a third feature; where the sum of attention weights of the two channels is equal to 1.

Step S230, the QRS complex is detected according to the third feature.

In the above steps, the features output by the two channels are fused by means of respective channel importance weights through the attention mechanism, which can improve the sensitivity of the model to the QRS complex, and enhance the attention of the model to key information, thereby further optimizing the performance of detecting the QRS complex. Moreover, in the process of model training, different types of signals can be processed more flexibly by automatically learning the importance weights among different channels, and the generation process of the weights is detailed in the following embodiments.

As shown in FIGS. 3 to 6, in some embodiments of the present disclosure, the method for detecting the QRS complex of the electrocardiogram signal is provided, which includes the following steps.

Figure 3:
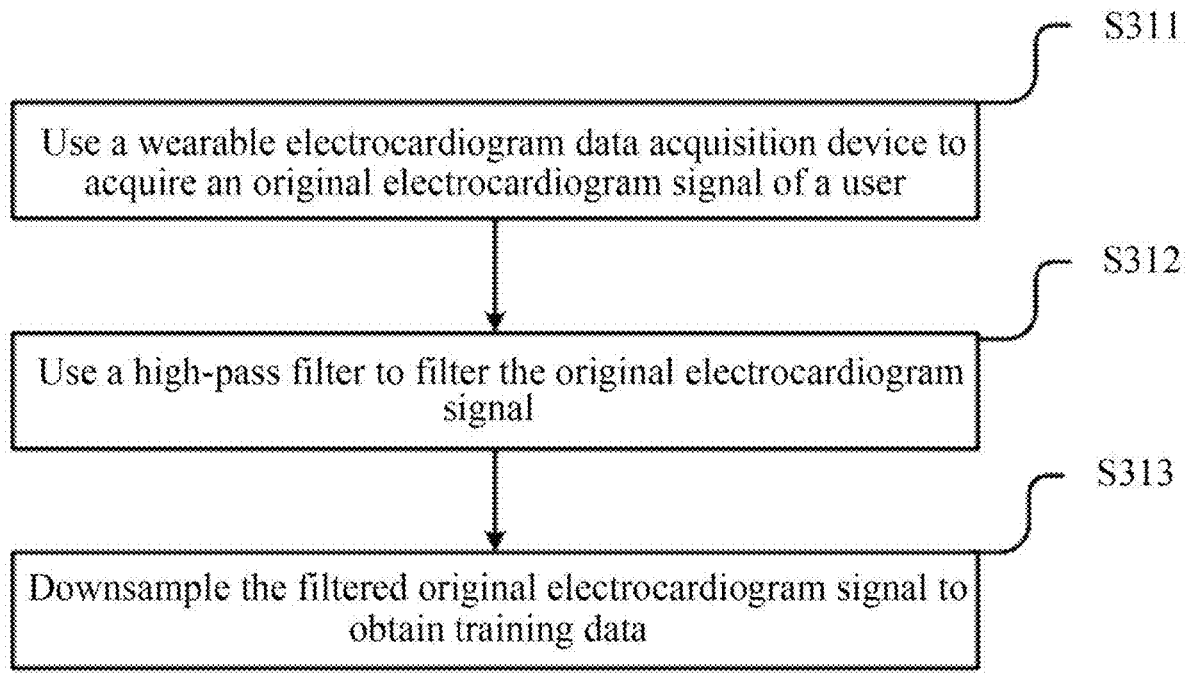
FIG. 3 is a schematic flow chart of acquiring training data according to an embodiment of the present disclosure.

Step S310, training data is acquired. As shown in FIG. 3, Step S310 includes Step S311 to Step S313.

Step S311, a wearable electrocardiogram data acquisition device is used to acquire an original electrocardiogram signal of a user. The limb lead I of the wearable electrocardiogram data acquisition device is taken as an example. If a lead electrode falls off, or is in a poor connection or suffers from other connection problems, the signal may be distorted and the data may be re-acquired.

Step S312, a high-pass filter is used to filter the original electrocardiogram signal. Step S312 is used to remove low frequency noise.

Step S313, the filtered original electrocardiogram signal is downsampled to obtain training data. Downsampling can reduce the computational burden and improve the computational efficiency, while retaining the key frequency information.

Figure 4:
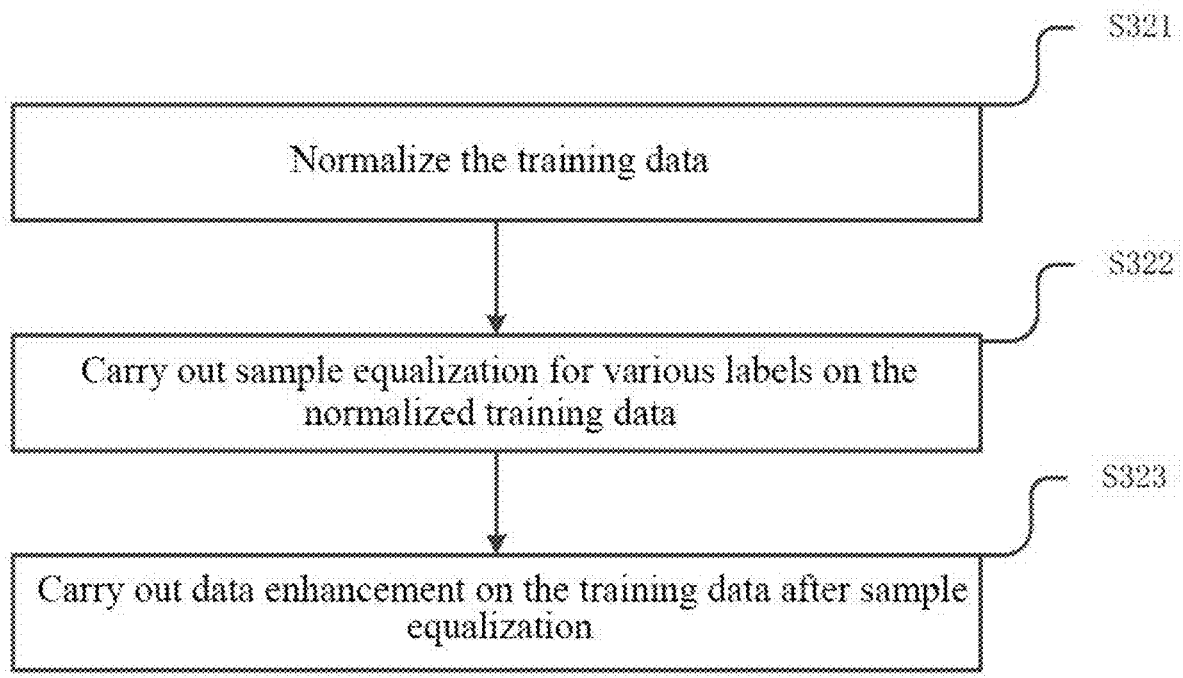
FIG. 4 is a flow chart of the preprocessing of training data according to an embodiment of the present disclosure.
Figure 5:
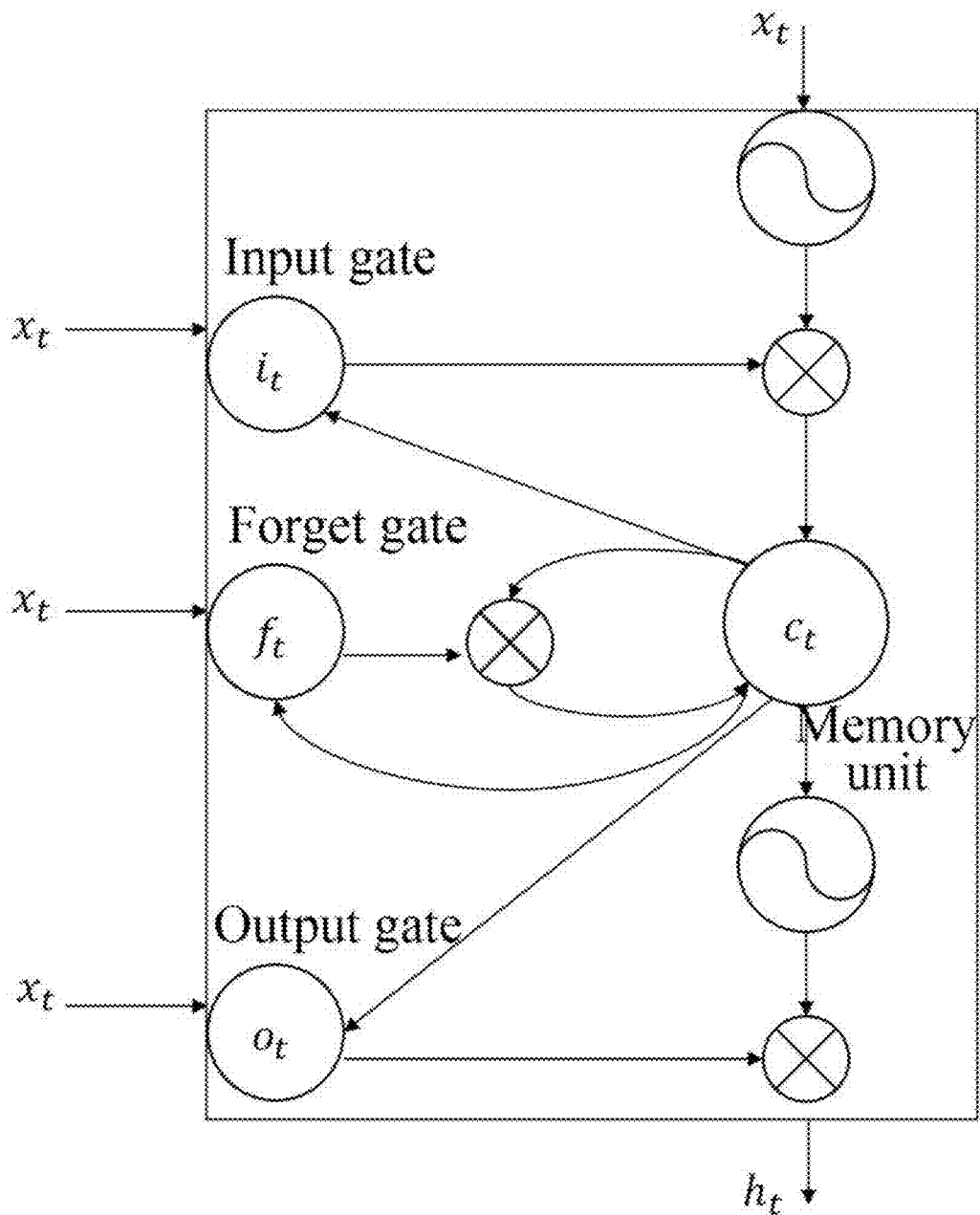
FIG. 5 is a schematic diagram of a structure of the LSTM according to an embodiment of the present disclosure.

Step S320, the training data is preprocessed. As shown in FIG. 4, the preprocessing of Step S320 includes Step S321 to Step S323.

Step S321, the training data is normalized.

In some embodiments, a Z-Score standardization method is used to linearly transform data according to its mean and standard deviation, so that the transformed data has a standard normal distribution with a mean of 0 and a standard deviation of 1. The transformation function is:

$$x_{new} = \frac{x - u}{\sigma}$$

where u is a sample mean, and $\sigma$ is a standard deviation of sample data. The normalized data keeps the useful information in outliers.

Step S322, sample equalization for various labels is carried out on the normalized training data.

In some embodiments, Step S322 includes Steps S3221-S3224.

Step S3221, minority category samples in the normalized training data are selected.

Step S3222, a corresponding neighbor is randomly selected for each of the minority category samples, where the neighbor is one of K nearest neighbor samples of each of the minority category samples. For each of the minority category samples, the K nearest neighbor samples are taken into account. Usually, the value of K is 3 or 5, which can be set according to experience.

Step S3223, a new sample is generated between each of the minority category samples and a corresponding neighbor by a linear interpolation method. Specifically, for each feature, a difference between the selected sample and its neighbors is calculated, and then the difference multiplied by a random number is added to the selected sample to generate a new composite sample.

Step S3224, repeat the above Step S3221 to Step S3223 until a predetermined data equalization degree is reached.

Step S323, data enhancement is carried out on the training data after sample equalization.

In this embodiment, the number of the minority category samples is increased by synthesizing new sample in minority category, so that the number of samples in different categories is more equalized. This can improve the learning effect of the model on the minority category, for better identification and classification.

Step S330, the detection model and the training process are designed.

Figure 6:
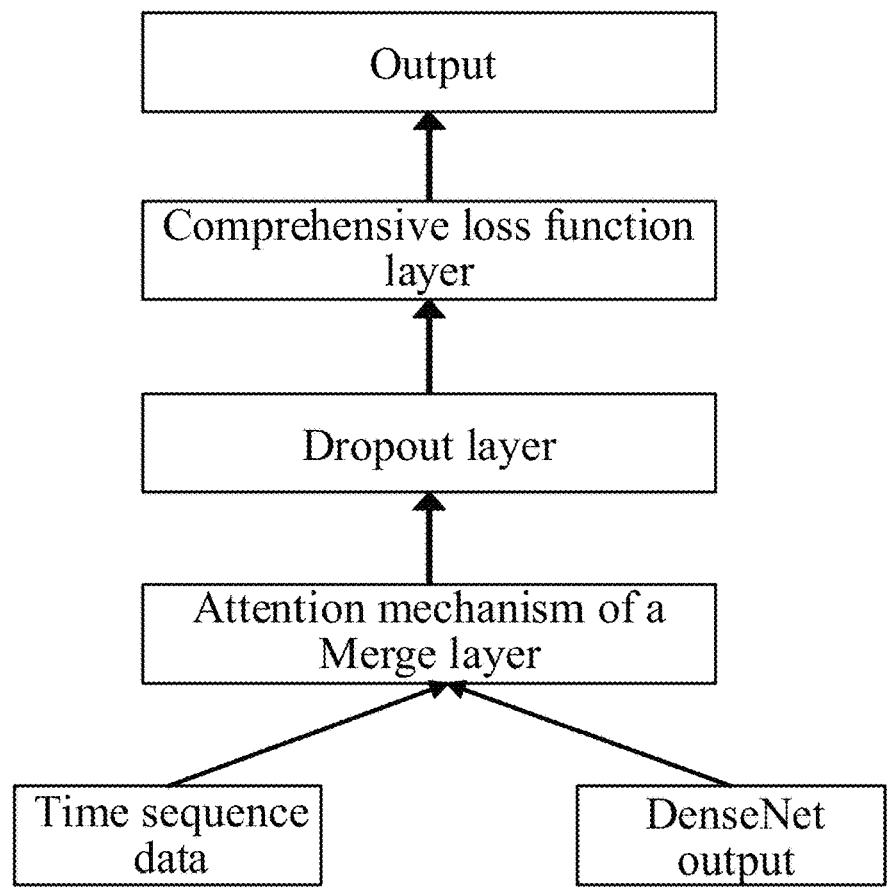
FIG. 6 is a flow chart of outputting a detection result by a dual-channel LSTM according to an embodiment of the present disclosure.

Referring to FIG. 6, a detection model including a DenseNet and a dual-channel LSTM is constructed. In some embodiments, the detection model is consisted of a DenseNet and a LSTM.

The preprocessed time sequence data is input into the DenseNet, and the DenseNet is responsible for extracting the spatial feature of the QRS complex from the preprocessed time sequence data. Thereafter, the time sequence data and the output feature of the DenseNet are input into the LSTM as two branches, so that the spatial and time sequence information can be more flexibly fused by the LSTM.

The preprocessed time sequence data is input into the detection model, and the corresponding label, which indicates whether there is a QRS complex, is provided. The model parameters are trained by back propagation and by an optimizer.

Selection of loss function. The QRS complex is detected and identified, comprehensive loss function is used, combining with the classification loss and the regression loss, to ensure that the model can detect the existence and position of the QRS complex. In some embodiments, the loss function of the detection model in the training process is:

$$L_{total}=L_{cls}+\lambda L_{reg};$$

$$L_{cls}(y_{cls},\hat{y}_{cls})=-(y_{cls}\cdot\log(\hat{y}_{cls})+(1-y_{cls})\cdot\log(1-\hat{y}_{cls}));$$

$$L_{reg}(t_{reg},\hat{t}_{reg})=\text{Smooth}L1(t_{reg}-\hat{t}_{reg});$$

where $L_{total}$ denotes a loss function of the detection model, $L_{cls}$ denotes a classification loss, $L_{reg}$ denotes a regression loss, $\lambda$ denotes a predetermined weight parameter for equalizing the classification loss and the regression loss, $\hat{y}_{cls}$ denotes the QRS complex detected by the detection model, $y_{cls}$ denotes a real category label, $\hat{t}_{reg}$ denotes the position of the QRS complex detected by the detection model, and $t_{reg}$ denotes a real position label.

Optimizer and learning rate strategy. Adaptive Moment Estimation (Adam) is an optimization algorithm of adaptive learning rate, which usually performs well in deep learning. The Adam combines the advantages of adaptive gradient (Adagrad, an optimization algorithm) and root mean square propagation (RMSProp), adapts to the learning rate of different parameters, and is helpful to deal with non-stationary objective functions.

The attention mechanism is set in the dual-channel LSTM, which is the same as the above Step S220, the detection model obtains the attention weight by the following equation:

$$\text{Attention}(H_{LSTM1},H_{LSTM2})=\text{softmax}(W\cdot\tanh(U\cdot H_{LSTM1}+V\cdot H_{LSTM2}));$$

where $H_{LSTM1}$ is an output feature of the first channel, $H_{LSTM2}$ is an output feature of the second channel, tanh is a hyperbolic tangent function, softmax( ) is an activation function, W, U, V are learnable weight parameters, and Attention($H_{LSTM1}$,$H_{LSTM2}$) is an attention weight;

in the training process, the detection model fuses the output feature of the first channel and the output feature of the second channel by the following equation:

$$\text{Fused Feature}=\text{Attention}(H_{LSTM1},H_{LSTM2})\cdot H_{LSTM1}+(1-\text{Attention}(H_{LSTM1},H_{LSTM2}))\cdot H_{LSTM2};$$

where Fused Feature is a feature obtained by fusing the output feature of the first channel and the output feature of the second channel.

Weighted fusion is performed on the features of the two channels by using the calculated attention weight, so that the fused features contain the information of the two channels and weigh importance of the two channels.

Referring to FIG. 6, the fused features are input to the subsequent layer of the LSTM for further processing.

Step S340, the model is evaluated.

The index for evaluating performance includes sensitivity (Se), positive prediction rate (+P) and accuracy rate (Acc), which are expressed as follow:

$$Se=\frac{TP}{TP+FN}+P=\frac{TP}{TP+FP}$$

$$Acc=\frac{TP}{TP+FP+FN}$$

where True Positive (TP) refers to the number of correctly classified positive samples, that is, the number of the QRS complex being correctly detected. False Positive (FP) refers to the number of negative samples wrongly marked as positive samples, that is, the number of the QRS complex being reported without the QRS complex. False Negative (FN) refers to the number of positive samples wrongly marked as negative samples, that is, the number of the QRS complex being missed.

Step S350, the detection model is used, and a recognition result is returned.

Referring to the above Step S110 and Step S120 for the use of the detection model, which will not be described in detail here. The identification results are sent to a cloud terminal and a user terminal. The medical data is archived in the cloud terminal for experts or doctors to check and further diagnose, and the user terminal provides identified QRS complex results of the electrocardiogram of a user.

One of the application scenarios of this embodiment is described hereinafter:

This method is suitable for an electrocardiogram automatic analysis system, which realizes automatic detection and analysis of the QRS complex, and is helpful to the next step of electrocardiogram (ECG) heartbeat segmentation, and helpful to disease prediction and classification according to various types of heartbeats. The automatic detection of the QRS complex in the electrocardiogram can help to carry out early cardiovascular disease screening, thereby finding abnormal situation in time and providing basis for early treatment. At the same time, this method can be used as a medical auxiliary tool to provide doctors with more comprehensive electrocardiogram information, thereby assisting in the diagnosis of cardiac diseases and abnormalities to provide reference for treatment plans. Combined with the portable wearable medical system, this method can be embedded in the portable wearable medical system to realize real-time and remote electrocardiogram monitoring, so that patients can manage their health conveniently.

In this embodiment, the DenseNet network structure is used to effectively extract the spatial feature of the QRS complex in the electrocardiogram, which enhances abstraction ability for the waveform shape; and the dual-channel LSTM is innovatively used to process the time sequence information, which helps the model to remember time sequence model of the QRS complex and better capture the dynamic changes of the QRS complex. By combining the DenseNet and the LSTM, the model can take into account both the spatial feature of images and the time sequence model of the time sequence, thus improving the accuracy and robustness of detecting the QRS complex. In this embodiment, an attention mechanism is also introduced, and weighted fusion is performed on the features of two channels in the dual-channel LSTM, which can improve detection sensitivity to the QRS complex, and can enhance the attention of the model to key information, thereby further optimizing the performance of detecting the QRS complex. This method has a wide application prospect in the field of heartbeat segmentation, electrocardiogram analysis, early diagnosis and treatment, etc., and is especially suitable for the portable wearable medical device, and provides new possibilities for future medical research and clinical experience.

Figure 7:
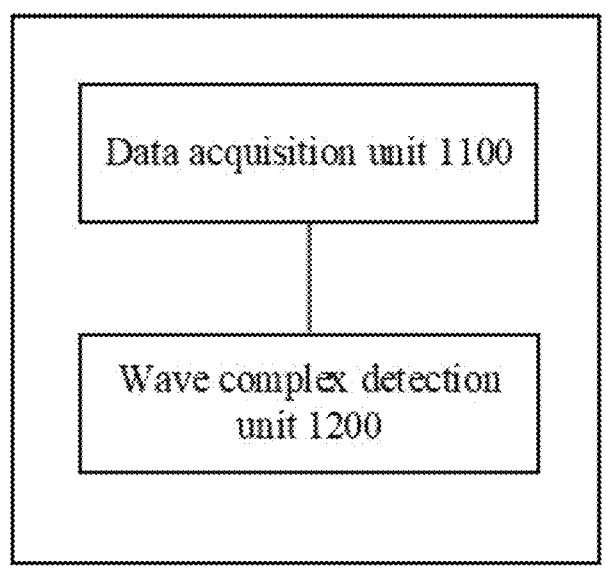
FIG. 7 is a schematic structural diagram of an apparatus for detecting a QRS complex of an electrocardiogram signal according to an embodiment of the present disclosure.

Referring to FIG. 7, an apparatus for detecting a QRS complex of an electrocardiogram signal according to an embodiment of the present disclosure, includes a data acquisition unit 1100 and a wave complex detection unit 1200.

The data acquisition unit 1100 is configured to acquire time sequence data of an electrocardiogram signal from an electrocardiogram signal;

The wave complex detection unit 1200 is configured to construct a detection model including a DenseNet and a dual-channel Long Short-Term Memory (LSTM), input the time sequence data into the detection model to extract a spatial feature of the electrocardiogram signal from the time sequence data according to the DenseNet, input the time sequence data and the spatial feature into a corresponding channel of the dual-channel LSTM, and detect a QRS complex of the electrocardiogram signal by the dual-channel LSTM. In some embodiments, the detection model is consisted of the DenseNet and the LSTM.

It should be noted that the apparatus for detecting the QRS complex of the electrocardiogram signal provided in this embodiment is based on the same inventive concept as the method for detecting the QRS complex embodiment of the electrocardiogram signal. Therefore, the related contents of the embodiment of the method for detecting the QRS complex of the electrocardiogram signal are also applicable to the embodiment of the apparatus for detecting the QRS complex of the electrocardiogram signal, which will not be described in detail here.

Figure 8:
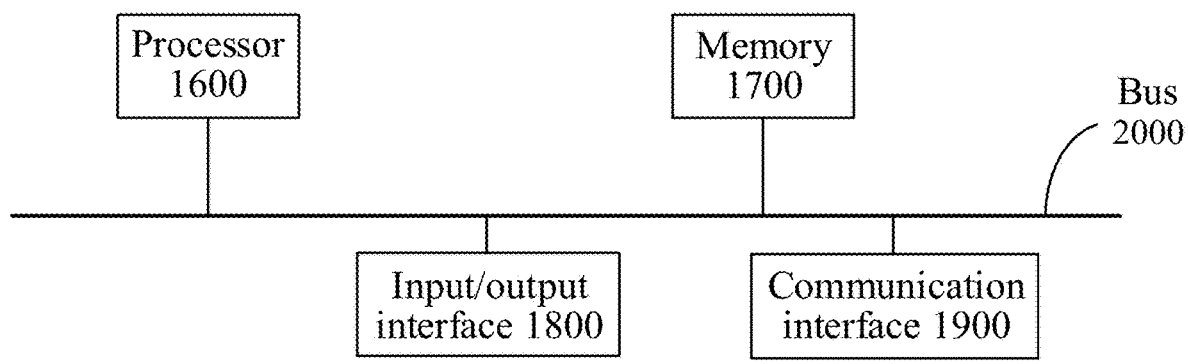
FIG. 8 is a schematic structural diagram of an electronic device according to an embodiment of the present disclosure.

As shown in FIG. 8, the embodiment of the present disclosure further provides an electronic device, which includes:

at least one memory;
at least one processor;
at least one program;
where the program is stored in the memory, and the processor executes at least one program to implement the method for detecting the QRS complex of the electrocardiogram signals described in the present disclosure.

The electronic device can be any intelligent terminal including a mobile phone, a tablet computer, a Personal Digital Assistant (PDA), a vehicle-mounted computer and so on.

The electronic device of the embodiment of the present disclosure will be described in detail hereinafter.

The processor 1600 can be implemented by a general Central Processing Unit (CPU), a microprocessor, an Application Specific Integrated Circuit (ASIC), or one or more integrated circuits, etc., and is used to execute relevant programs to implement the technical scheme according to the embodiment of the present disclosure.

The memory 1700 can be implemented in the form of a Read Only Memory (ROM), a static storage device, a dynamic storage device or a Random Access Memory (RAM). The memory 1700 can store the operating system and other application programs. When the technical scheme according to the embodiment of this specification is implemented by software or firmware, the relevant program codes are stored in the memory 1700, and the processor 1600 calls the relevant program codes to implement the method for detecting the QRS complex of the electrocardiogram signal according to the embodiment of the present disclosure.

An input/output interface 1800 is configured to input and output information.

A communication interface 1900 is configured to realize the communication interaction between the device and other devices, and can realize communication by wired means (such as a USB, a network cable, etc.) or wireless means (such as a mobile network, WIFI, Bluetooth, etc.).

A bus 2000 is configured to transmit information among various components of the device (for example, the processor 1600, the memory 1700, the input/output interface 1800 and the communication interface 1900).

The processor 1600, the memory 1700, the input/output interface 1800 and the communication interface 1900 realize the communication connection with each other in the device through the bus 2000.

The embodiment of the present disclosure further provides a storage medium, which is a computer-readable storage medium. Computer-executable instructions are stored in the computer-readable storage medium, and the computer-executable instructions are used to cause a computer to execute the method for detecting the QRS complex of the electrocardiogram signal.

As a non-transient computer-readable storage medium, the memory can be used to store non-transient software programs and non-transient computer-executable programs. In addition, the memory may include a high-speed random access memory and a non-transient memory, such as at least one disk memory device, a flash memory, or other non-transient solid-state memory devices. In some embodiments, the memory may be selected memories including remotely located with respect to the processor, and these remote memories may be connected to the processor through a network. Examples of the above networks include, but are not limited to, the Internet, an enterprise intranet, a local area network, a mobile communication network, and a combination thereof.

The embodiment described in the present disclosure is to explain the technical scheme of the embodiment of the present disclosure more clearly, and does not constitute the limitation of the technical scheme provided by the embodiment of the present disclosure. As known as those skilled in the art, with the technical evolution and the emergence of new application scenarios, the technical scheme provided by the embodiment of the present disclosure is also applicable to similar technical problems.

It can be understood by those skilled in the art that the technical scheme shown in the figure does not constitute a limitation to the embodiment of the present disclosure, and may include more or less steps than those shown in the figures, or combine some steps or different steps.

The apparatus embodiments described above are only schematic, in which the units described as separate components may or may not be physically separated, that is, they may be located in one place or may be distributed to a plurality of network units. Some or all of the modules can be selected according to actual needs to achieve the purpose of the scheme of this embodiment.

Those skilled in the art can understand that all or some of the functional modules/units in the steps, systems and methods disclosed above can be implemented as software, firmware, hardware and the appropriate combination thereof.

The terms "first", "second", "third" and "fourth" in the specification of the present disclosure and the above drawings, if any, are used to distinguish similar objects, and are not necessarily used to describe a specific order or sequence. It should be understood that the data used in this way can be interchanged where appropriate, so that the embodiments of the present disclosure described herein can be implemented in other orders than those illustrated or described herein. Furthermore, the terms "including" and "having" and any variations thereof are intended to cover non-exclusive inclusion. For example, a process, method, system, product or device that includes a series of steps or units is not necessarily limited to those steps or units explicitly listed, but may include other steps or units not explicitly listed or inherent to such processes, methods, products or devices.

It should be understood that in the present disclosure, "at least one (item)" means one or more, and "a plurality of" means two or more. "and/or" is used to describe the association relationship of associated objects, indicating that there can be three relationships. For example, "A and/or B" can indicate that there are only A, only B and both A and B, where A and B can be singular or plural. The character "/" generally indicates that the context object is an "or" relationship. "At least one of the following items" or its similar expression refers to any combination of these items, including any combination of single items or plural items. For example, at least one of a, b or c can be expressed as: a, b, c, "a and b", "a and c", "b and c", or "a and b and c", where a, b and c can be singular or plural.

In several embodiments provided by the present disclosure, it should be understood that the disclosed apparatuses and methods can be implemented in other ways. For example, the apparatus embodiment described above is only schematic. For example, the division of units is only a logical function division. In actual implementation, there may be other division methods, such as a plurality of units or components can be combined or integrated into another system, or some features can be ignored or not implemented. On the other hand, the mutual coupling or direct coupling or communication connection shown or discussed can be indirect coupling or communication connection through some interfaces, apparatuses or units, which can be electrical, mechanical or in other forms.

The units described as separate components may or may not be physically separated, and the components displayed as units may or may not be physical units, that is, that is, they may be located in one place or may be distributed to a plurality of network units. Some or all of the modules can be selected according to actual needs to achieve the purpose of the scheme of this embodiment.

In addition, each functional unit in each embodiment of the present disclosure can be integrated into one processing unit, or each unit can exist physically alone, or two or more units can be integrated into one unit. The above integrated units can be implemented in the form of hardware or software functional units.

The integrated units can be stored in a computer-readable storage medium if they are implemented in the form of software functional units and sold or used as independent products. Based on this understanding, the technical scheme of the present disclosure in essence, or the part that contributes to the prior art, or all or part of the technical scheme can be embodied in the form of software products, which are stored in a storage medium and include a plurality of instructions so that an electronic device (which can be a personal computer, a server, a network apparatus, etc.) executes all or part of the steps of the methods of various embodiments of the present disclosure. The above storage media include media that can store programs, such as a USB flash disk, a mobile hard disk, a Read-Only Memory (ROM), a Random Access Memory (RAM), a magnetic disk or an optical disk.

The above is a detailed description of the preferred implementation of the embodiment of the present disclosure, but the embodiment of the present disclosure is not limited to the above-mentioned implementation. Those skilled in the art may make various equivalent modifications or substitutions without violating the spirit of the embodiments of the present disclosure, which are included in the scope defined by the claims of the embodiment of the present disclosure.

What is claimed is:

1. A method for detecting a QRS complex of an electrocardiogram signal, comprising:
   acquiring time sequence data of the electrocardiogram signal from an electrocardiogram signal;
   constructing a detection model consisting of a DenseNet and a dual-channel Long Short-Term Memory (LSTM), inputting the time sequence data into the detection model to extract a spatial feature of the electrocardiogram signal from the time sequence data according to the DenseNet, inputting the time sequence data and the spatial feature into respective channels of the dual-channel LSTM, and detecting a QRS complex of the electrocardiogram signal by the dual-channel LSTM;
   wherein the inputting the time sequence data and the spatial feature into respective channels of the dual-channel LSTM, and detecting a QRS complex of the electrocardiogram signal by the dual-channel LSTM, comprises:
   inputting the time sequence data into a first channel of the dual-channel LSTM to obtain a first feature output by the first channel, and inputting the spatial feature into a second channel of the dual-channel LSTM to obtain a second feature output by the second channel;
   fusing the first feature and the second feature by means of respective attention weights by using an attention mechanism to obtain a third feature; wherein a sum of attention weights of two channels is equal to 1;

detecting the QRS complex according to the third feature;
wherein the detection model is trained by preprocessed training data; and preprocessing of training data comprises:
  normalizing the training data;
  carrying out sample equalization for various labels on normalized training data;
  carrying out data enhancement on the training data after sample equalization;
wherein in training process, the detection model obtains the attention weights by following equation:

$$\text{Attention}(H_{LSTM1},H_{LSTM2})=\text{softmax}(W\cdot\tanh(U\cdot H_{LSTM1}+V\cdot H_{LSTM2}));$$

wherein $H_{LSTM1}$ is an output feature of the first channel, $H_{LSTM2}$ is an output feature of the second channel, tanh is a hyperbolic tangent function, softmax( ) is an activation function, W, U, V are learnable weight parameters, and Attention($H_{LSTM1}$,$H_{LSTM2}$) is the attention weights;
wherein in the training process, the detection model fuses the output feature of the first channel and the output feature of the second channel by following equation:

$$\text{Fused Feature}=\text{Attention}(H_{LSTM1},H_{LSTM2})\cdot H_{LSTM1}+(1-\text{Attention}(H_{LSTM1},H_{LSTM2}))\cdot H_{LSTM2};$$

wherein Fused Feature is a feature obtained by fusing the output feature of the first channel and the output feature of the second channel.

2. The method according to claim 1, wherein the carrying out sample equalization for various labels on normalized training data comprises:
  repeating following steps until a predetermined data equalization degree is reached; the following steps comprise:
    selecting minority category samples in the normalized training data;
    randomly selecting a corresponding neighbor for each of the minority category samples, wherein the neighbor is one of several nearest neighbor samples of each of the minority category samples;
    generating a new sample between each of the minority category samples and corresponding neighbor by a linear interpolation method.

3. The method according to claim 1, wherein a loss function of the detection model in the training process is:

$$L_{total}=L_{cls}+\lambda L_{reg};$$

$$L_{cls}(y_{cls},\hat{y}_{cls})=-(y_{cls}\cdot\log(\hat{y}_{cls})+(1-y_{cls})\cdot\log(1-\hat{y}_{cls}));$$

$$L_{reg}(t_{reg},\hat{t}_{reg})=\text{Smooth}L1(t_{reg}-\hat{t}_{reg});$$

where $L_{total}$ denotes a loss function of the detection model, $L_{cls}$ denotes a classification loss, $L_{reg}$ denotes a regression loss, $\lambda$ denotes a predetermined weight parameter, $\hat{y}_{cls}$ denotes the QRS complex detected by the detection model, $y_{cls}$ denotes a real category label, $\hat{t}_{reg}$ denotes a position of the QRS complex detected by the detection model, and $t_{reg}$ denotes a real position label.

4. The method according to claim 1, wherein the training data is obtained by following steps:
  using a wearable electrocardiogram data acquisition device to acquire an original electrocardiogram signal of a user;
  using a high-pass filter to filter the original electrocardiogram signal;
  downsampling the original electrocardiogram signal filtered to obtain the training data.

5. An electronic device, comprising at least one control processor and a memory communicated with the at least one control processor; wherein instructions executable by the at least one control processor are stored in the memory, and the instructions are executed by the at least one control processor, so that the at least one control processor is capable of executing the method for detecting the QRS complex of the electrocardiogram signal according to claim 1.

6. The electronic device according to claim 5, the instructions are executed by the at least one control processor, so that the at least one control processor is capable of executing following steps:
  repeating following steps until a predetermined data equalization degree is reached; the following steps comprise:
    selecting minority category samples in the normalized training data;
    randomly selecting a corresponding neighbor for each of the minority category samples, wherein the neighbor is one of several nearest neighbor samples of each of the minority category samples;
    generating a new sample between each of the minority category samples and corresponding neighbor by a linear interpolation method.

7. The electronic device according to claim 5, wherein a loss function of the detection model in the training process is:

$$L_{total}=L_{cls}+\lambda L_{reg};$$

$$L_{cls}(y_{cls},\hat{y}_{cls})=-(y_{cls}\cdot\log(\hat{y}_{cls})+(1-y_{cls})\cdot\log(1-\hat{y}_{cls}));$$

$$L_{reg}(t_{reg},\hat{t}_{reg})=\text{Smooth}L1(t_{reg}-\hat{t}_{reg});$$

where $L_{total}$ denotes a loss function of the detection model, $L_{cls}$ denotes a classification loss, $L_{reg}$ denotes a regression loss, $\lambda$ denotes a predetermined weight parameter, $\hat{y}_{cls}$ is denotes the QRS complex detected by the detection model, $y_{cls}$ denotes a real category label, $\hat{t}_{reg}$ denotes a position of the QRS complex detected by the detection model, and $t_{reg}$ denotes a real position label.

8. The electronic device according to claim 5, wherein the training data is obtained by following steps:
  using a wearable electrocardiogram data acquisition device to acquire an original electrocardiogram signal of a user;
  using a high-pass filter to filter the original electrocardiogram signal;
  downsampling the original electrocardiogram signal filtered to obtain the training data.

9. A non-transitory computer-readable storage medium, wherein computer-executable instructions are stored in the non-transitory computer-readable storage medium, and the computer-executable instructions are used to cause a computer to execute the method for detecting the QRS complex of the electrocardiogram signal according to claim 1.

10. The non-transitory computer-readable storage medium according to claim 9, the computer-executable instructions are used to cause a computer to execute following steps:
  repeating following steps until a predetermined data equalization degree is reached; the following steps comprise:
    selecting minority category samples in the normalized training data;

randomly selecting a corresponding neighbor for each of the minority category samples, wherein the neighbor is one of several nearest neighbor samples of each of the minority category samples;

generating a new sample between each of the minority category samples and corresponding neighbor by a linear interpolation method.

11. The non-transitory computer-readable storage medium according to claim 9, wherein a loss function of the detection model in the training process is:

$$L_{total}=L_{cls}+\lambda L_{reg};$$

$$L_{cls}(y_{cls},\hat{y}_{cls})=-(y_{cls}\cdot\log(\hat{y}_{cls})+(1-y_{cls})\cdot\log(1-\hat{y}_{cls}));$$

$$L_{reg}(t_{reg},\hat{t}_{reg})=\text{Smooth}L1(t_{reg}-\hat{t}_{reg});$$

where $L_{total}$ denotes a loss function of the detection model, $L_{cls}$ denotes a classification loss, $L_{reg}$ denotes a regression loss, $\lambda$ denotes a predetermined weight parameter, $\hat{y}_{cls}$ denotes the QRS complex detected by the detection model, $y_{cls}$ denotes a real category label, $\hat{t}_{reg}$ denotes a position of the QRS complex detected by the detection model, and $t_{reg}$ denotes a real position label.

12. The non-transitory computer-readable storage medium according to claim 9, wherein the training data is obtained by following steps:

using a wearable electrocardiogram data acquisition device to acquire an original electrocardiogram signal of a user;

using a high-pass filter to filter the original electrocardiogram signal;

downsampling the original electrocardiogram signal filtered to obtain the training data.

13. An apparatus for detecting a QRS complex of an electrocardiogram signal, wherein the apparatus comprises:

a data acquisition unit, configured for acquiring time sequence data of the electrocardiogram signal from the electrocardiogram signal;

a wave complex detection unit, configured for constructing a detection model consisting of DenseNet and a dual-channel Long Short-Term Memory (LSTM), inputting the time sequence data into the detection model to extract a spatial feature of the electrocardiogram signal from the time sequence data according to the DenseNet, inputting the time sequence data and the spatial feature into respective channels of the dual-channel LSTM, and detecting a QRS complex of the electrocardiogram signal by the dual-channel LSTM;

wherein the inputting the time sequence data and the spatial feature into respective channels of the dual-channel LSTM, and detecting a QRS complex of the electrocardiogram signal by the dual-channel LSTM, comprises:

inputting the time sequence data into a first channel of the dual-channel LSTM to obtain a first feature output by the first channel, and inputting the spatial feature into a second channel of the dual-channel LSTM to obtain a second feature output by the second channel;

fusing the first feature and the second feature by means of respective attention weights by using an attention mechanism to obtain a third feature; wherein a sum of attention weights of two channels is equal to 1;

detecting the QRS complex according to the third feature;

wherein the detection model is trained by preprocessed training data; and preprocessing of training data comprises:

normalizing the training data;

carrying out sample equalization for various labels on normalized training data;

carrying out data enhancement on the training data after sample equalization;

wherein in training process, the detection model obtains the attention weights by following equation:

$$\text{Attention}(H_{LSTM1},H_{LSTM2})=\text{softmax}(W\cdot\tanh(U\cdot H_{LSTM1}+V\cdot H_{LSTM2}));$$

wherein $H_{LSTM1}$ is an output feature of the first channel, $H_{LSTM2}$ is an output feature of the second channel, tanh is a hyperbolic tangent function, softmax( ) is an activation function, W, U, V are learnable weight parameters, and Attention($H_{LSTM1}$,$H_{LSTM2}$) is the attention weights;

wherein in the training process, the detection model fuses the output feature of the first channel and the output feature of the second channel by following equation:

$$\text{Fused Feature}=\text{Attention}(H_{LSTM1},H_{LSTM2})\cdot H_{LSTM1}+(1-\text{Attention}(H_{LSTM1},H_{LSTM2}))\cdot H_{LSTM2};$$

wherein Fused Feature is a feature obtained by fusing the output feature of the first channel and the output feature of the second channel.

* * * * *